(12) United States Patent
Fronabarger et al.

(10) Patent No.: US 8,524,019 B2
(45) Date of Patent: Sep. 3, 2013

(54) ALTERNATIVE TO TETRAZENE

(75) Inventors: John W. Fronabarger, Sun Lakes, AZ (US); Michael D. Williams, Gilbert, AZ (US)

(73) Assignee: Pacific Scientific Energetic Materials Company, Chandler, AZ (US)

( * ) Notice: Subject to any disclaimer, the term of this patent is extended or adjusted under 35 U.S.C. 154(b) by 94 days.

(21) Appl. No.: 13/091,708

(22) Filed: Apr. 21, 2011

(65) Prior Publication Data

US 2012/0145290 A1 Jun. 14, 2012

Related U.S. Application Data

(60) Provisional application No. 61/326,768, filed on Apr. 22, 2010, provisional application No. 61/370,563, filed on Aug. 4, 2010.

(51) Int. Cl.
*D03D 43/00* (2006.01)

(52) U.S. Cl.
USPC ............... 149/92; 149/2; 149/88; 149/108.6; 149/109.4; 149/109.6

(58) Field of Classification Search
USPC ............... 149/92, 2, 88, 108.6, 109.4, 109.6
See application file for complete search history.

(56) References Cited

U.S. PATENT DOCUMENTS

| | | | | |
|---|---|---|---|---|
| 4,023,352 A | * | 5/1977 | Sayles | 60/218 |
| 4,564,659 A | * | 1/1986 | Kataoka et al. | 525/328.2 |
| 5,216,199 A | | 6/1993 | Bjerke et al. | |
| 5,436,357 A | * | 7/1995 | Jiang et al. | 556/95 |
| 5,717,159 A | * | 2/1998 | Dixon et al. | 149/40 |
| 6,004,411 A | * | 12/1999 | Zeuner et al. | 149/78 |
| 6,964,287 B1 | * | 11/2005 | Nesveda et al. | 149/19.8 |
| 2009/0151825 A1 | | 6/2009 | Bass | |

FOREIGN PATENT DOCUMENTS

| | | |
|---|---|---|
| FR | 1582964 A | 10/1969 |
| FR | 2897864 A1 | 8/2007 |
| GB | 201009 A | 7/1923 |
| GB | 412460 A | 6/1934 |
| WO | 2012003031 A3 | 5/2012 |

OTHER PUBLICATIONS

International Search Report and Written Opinion dated Mar. 15, 2012 in Application No. PCT/US2011/033356.
Bird and Power, "Thermal Decomposition of Tetrazene at 90°C," *Materials Research Laboratories Report*, MRL-R-710, 22 pages (1978).

(Continued)

*Primary Examiner* — James McDonough
(74) *Attorney, Agent, or Firm* — Dean W. Russell; Tiffany L. Williams; Kilpatrick Townsend & Stockton LLP

(57) ABSTRACT

Embodiments of materials suitable for use as a replacement for Tetrazene and methods of preparing such materials are described. In one embodiment, the material comprises MTX-1, as well as simple salts or complexes derived therefrom. The methods of preparing such materials include combining Tetrazene and an acid to form a suspension, where the acid is nitric acid, sulfuric acid, perchloric acid, or hydrochloric acid. A nitrite salt may be added to the suspension, where the nitrite salt is sodium nitrite, lithium nitrite, potassium nitrite, an aqueous solution of sodium nitrite, an aqueous solution of lithium nitrite, or an aqueous solution of potassium nitrite. In some embodiments, the suspension is stirred until the suspension has a white appearance.

11 Claims, 9 Drawing Sheets

(56) References Cited

OTHER PUBLICATIONS

Bird, "The Stab Sensitising Action of Tetrazene," *Materials Research Laboratories Technical Note* 362, 20 pages (1975).
Cooper, *Explosives Engineering*, Wiley-VCH New York, pp. 323-326 (1996).
Duke, "X-Ray Crystal and Molecular Structure of Tetrazene, ('Tetracene') $C_2H_8N_{10}O$" *Chemical Communications*, 2-3 (1971).
Field, "Hot Spot Ignition Mechanisms for Explosives," *Acc. Chem. Res.*, 25:489-496 (1992).
Gash, et al.,"Environmentally Benign Stab Detonators," LLNL Report PP-1362, UCRL-TR-201628, pp. I-II, 1-17 (2003).
Hoffman and Roth, *Ber. Dt. Chem. Ges.*, 43:682 (1910).
Kaye, et al., *Encyclopedia of Explosives and Related Items*, US Army ARDEC, 8: p. 373-p. 376 (1978).
Mehta, "Performance Testing of Lead Free Stab Detonators,"Presented at NDIA Fuze Conference, Norfolk, VA, 17 pages, May 11, 2006.
Spear and Elischer, "Studies on Stab Initiation. Sensitization of Lead Azide by Energetic Sensitizers," *Aust. J. Chem.*, 35:1-13 (1982).
Whelan, et al., The Kinetics and Thermochemistry of the Thermal Decomposition of the Initiating Explosive, Tetrazene,near its Ignition Temperature (between 385K and 400K), DSTO Aeronautical and Maritime Research Laboratory Report DSTO-TR-0450, 34 pages (1996).
International Preliminary Report on Patentability dated Nov. 1, 2012 in Application No. PCT/US2011/033356.

* cited by examiner

ALTERNATIVE TO TETRAZENE

CROSS-REFERENCE TO RELATED APPLICATIONS

This application claims the benefit of U.S. Provisional Patent Application Ser. No. 61/326,768, entitled "Alternatives to Tetrazene," filed Apr. 22, 2010, and claims the benefit of U.S. Provisional Patent Application Ser. No. 61/370,563, entitled "Alternative to Tetrazene," filed Aug. 4, 2010, the entire contents of each of which are incorporated herein by these references.

STATEMENT OF GOVERNMENT SUPPORT

This invention was made in part with U.S. government support under Contract No. N00014-09-M-0433 awarded by the United States of America for the Department of the Navy. The government has certain rights in this invention.

FIELD OF THE INVENTION

This invention relates to explosives, and in particular to preparation of a primer sensitizer.

BACKGROUND 1-amino-1(1H-tetrazol-5-yl)-azo-guanidine hydrate ("Tetrazene," 1, Scheme 1) is widely used in ordnance systems as a sensitizer of primer mixes for use in both percussion and stab applications.

Scheme 1:

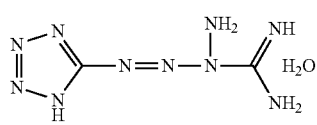

It has low thermal and hydrolytic stability compared with other components of primer mixes and there currently exists the need for a replacement with enhanced stability characteristics.

This material was initially prepared in 1910 by Hoffman and Roth, *Ber. Dtsch. Chem. Ges.*, 43, 682 (1910), and the molecular structure was determined in 1971. Duke, J. R. C., "X-Ray Crystal and Molecular Structure of Tetrazene", *J. Chem. Soc. D Chemical Communications*, 2 (1971). Tetrazene was first used in primer compositions in Germany in the 1920s due primarily to the work of Von Herz who demonstrated it to be non-corrosive as well as free of the toxic mercury fulminate used up to that time. In the United States, mercury fulminate-based primers were initially replaced with FA70, which contained potassium chlorate, lead thiocyanate and TNT. Fedoroff, *Encyclopedia of Explosives and Related Items*, Vol. 8, P373 (S. M. Kaye ed., US Army ARDEC 1978). These compositions, although useful for high temperature applications, also proved corrosive and were replaced in 1948 by FA956, which was developed by Rathsburg and contained Tetrazene and lead styphnate.

Current primer mixes, such as NOL-130, are generally comprised of basic lead styphnate 40%, lead azide 20%, barium nitrate 20%, antimony sulfide 15%, and Tetrazene 5%. Cooper, P. W., *Explosives Engineering*, 323-326 (Wiley-VCH, New York, 1996). However, mixes containing other components are known. Id. (teaching use of VH2 and L Mix); Federoff, supra (teaching use of PA100).

The NOL-130 composition is relatively insensitive to stab initiation when the Tetrazene component is omitted. The addition of ≧2% Tetrazene is currently a requirement to ensure high stab sensitivity. It has been proposed that the low mechanical energy requirements for initiation of Tetrazene-based compositions is a direct result of its low temperature of ignition (143° C.) in conjunction with its metastable chemical structure. Bird, R., "The Stab Sensitizing Action of Tetrazene," *Materials Research Laboratories Technical Note*, 362 (1975). This may be related to the mechanism of initiation where mechanical energy is applied to the primer and is converted to heat by friction and impact events between the explosive materials and/or grits in the composition. Field, J., "Hot Spot Ignition Mechanisms for Explosives," *Acc. Chem. Res.*, 25, 489 (1992). Spear and Elischer have investigated 17 compounds as alternates to Tetrazene for sensitizing lead azide. Spear, R. J. and Elischer, P. P., "Studies on Stab Initiation. Sensitization of Lead Azide by Energetic Sensitizers", *Aust. J. Chem.*, 35, 1 (1982). They correlated ignition temperature with initiation energies.

Tetrazene suffers from a number of issues, most importantly low thermal and hydrolytic stabilities. It has been demonstrated that Tetrazene readily decomposes at approximately 90° C., which is in the temperature range that may be encountered during storage and handling in some parts of the world. As illustrated in Scheme 2 below, Bird has demonstrated using IR and UV monitoring that at 90° C., 1 mol of Tetrazene decomposes to afford 1.7 mol of 5-aminotetrazole (2, Scheme 2) via a fragmentation process followed by cyclization of a majority of the guanyl azide intermediate. Bird, R. and Power, A. J., "Thermal Decomposition of Tetrazene at 90° C.," *Materials Research Laboratories Report MRL-R-710* (1978).

Scheme 2:

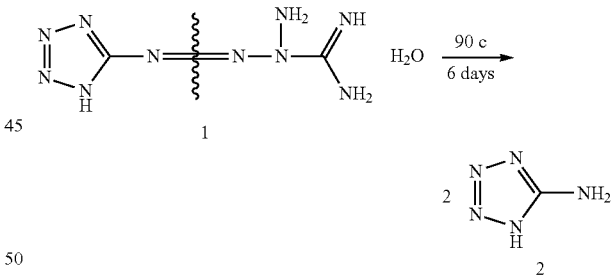

This decomposition is complete after 1 week at 90° C. and appears to be auto-catalytic. Thus, it is reasonable to presume that it will occur to some extent at lower temperatures. More recent investigations have confirmed these results. Whelan, D. J. and Fitzgerald, M. R., "The Kinetics and Thermochemistry of the Thermal Decomposition of the Initiating Explosive, Tetrazene," *DSTO Aeronautical and Maritime Research Laboratory Report DSTO-TR*-0450 (1996). Tetrazene has also been shown to be susceptible to hydrolytic decomposition and is destroyed/decomposed simply by addition to boiling water. Spear and Elischer, supra.

As a result, it is clear that there is a need to develop a stab sensitive material with improved thermal stability for primers used in normal or high temperature applications. In light of current environmental concerns, it may also be desirable to generate this new material both inexpensively and without the use of toxic materials as reactants or effluents.

SUMMARY

Embodiments of the invention provide materials suitable for use as a replacement for Tetrazene and methods of preparing such materials. In one embodiment, the material comprises MTX-1, as well as simple salts or complexes derived therefrom. In some embodiments, this material may be used in a primer composition.

In some embodiments, a method of preparing a material suitable for use as a replacement for Tetrazene includes combining Tetrazene and an acid to form a suspension, where the acid is nitric acid, sulfuric acid, perchloric acid, or hydrochloric acid, and adding a nitrite salt to the suspension, where the nitrite salt may include sodium nitrite, lithium nitrite, potassium nitrite, an aqueous solution of sodium nitrite, an aqueous solution of lithium nitrite, or an aqueous solution of potassium nitrite. The method may also include stirring the suspension. In some embodiments, the suspension is stirred for at least four hours or until the suspension has a white appearance.

DETAILED DESCRIPTION

Embodiments of the invention provide materials suitable for use as a replacement for Tetrazene and methods of preparing such materials. While the Tetrazene replacement materials are discussed for use in primer compositions, they are by no means so limited. Rather, the materials may be used as a replacement for Tetrazene in other applications or otherwise as desired.

A possible alternative to Tetrazene is shown in Scheme 3 below. This material, 1-[(2E)-3-(1H-tetrazol-5-yl)triaz-2-en-1-ylidene]methanediamine ("MTX-1", 3, Scheme 3), may be considered a Tetrazene derivative and is conveniently prepared from Tetrazene in one step in an aqueous solution.

Scheme 3:

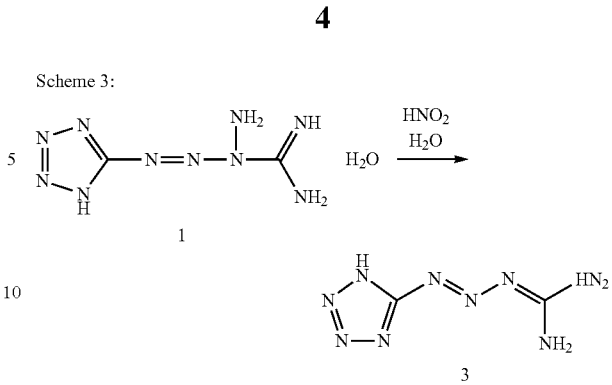

Figure 1:
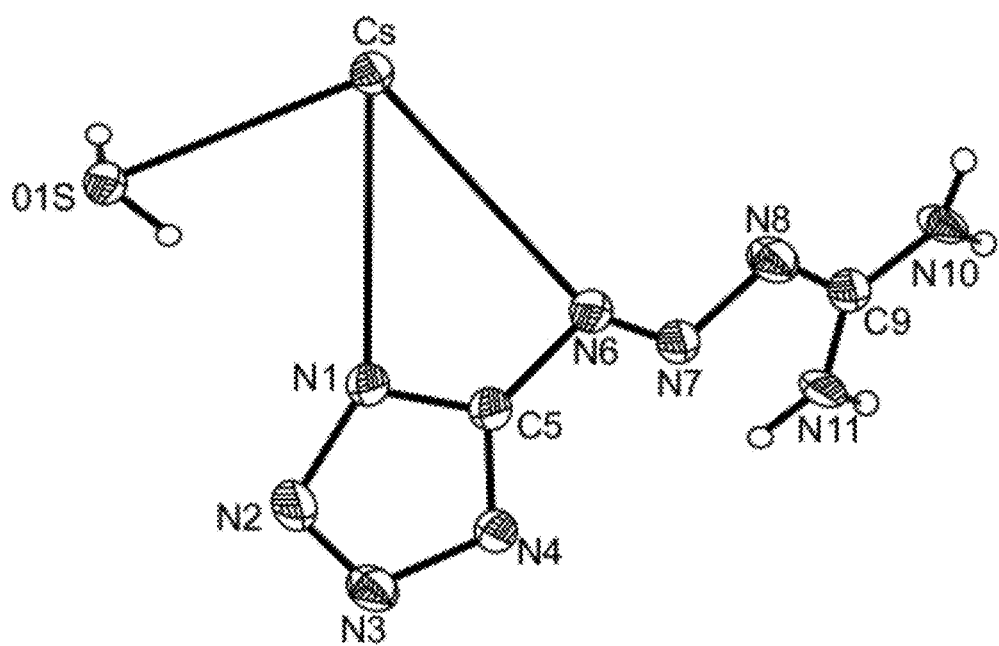
FIG. 1 shows the results of an X-ray analysis of a material prepared according to the present techniques.

The molecular structure of MTX-1 was determined by single crystal X-ray analyses of both the cesium, rubidium, and tetraphenylphosphonium salts obtained from slow recrystallization in aqueous solution. The displacement ellipsoid plot for the cesium salt is shown in FIG. 1. As illustrated in Scheme 3 above, MTX-1 is presumably formed via elimination of nitrous oxide from the labile N-nitrosamine intermediate generated by reaction of nitrous acid.

The hydrolytic stability of Tetrazene and MTX-1 were evaluated by UV analysis of a water solution of each material over an extended time period. The samples (approximately 0.50 g, accurately weighted and suspended in 250 mL of water) were stirred at room temperature to fully homogenize for the initial 8 hr period after which they were stirred briefly just prior to obtaining the spectra. The samples were filtered before acquisition of the UV spectra and the samples were returned to the bulk solution to maintain the concentration after sampling. The UV spectra for both Tetrazene and MTX-1 are shown in FIGS. 2 and 3, respectively, with the noted sampling times.

Figure 2:
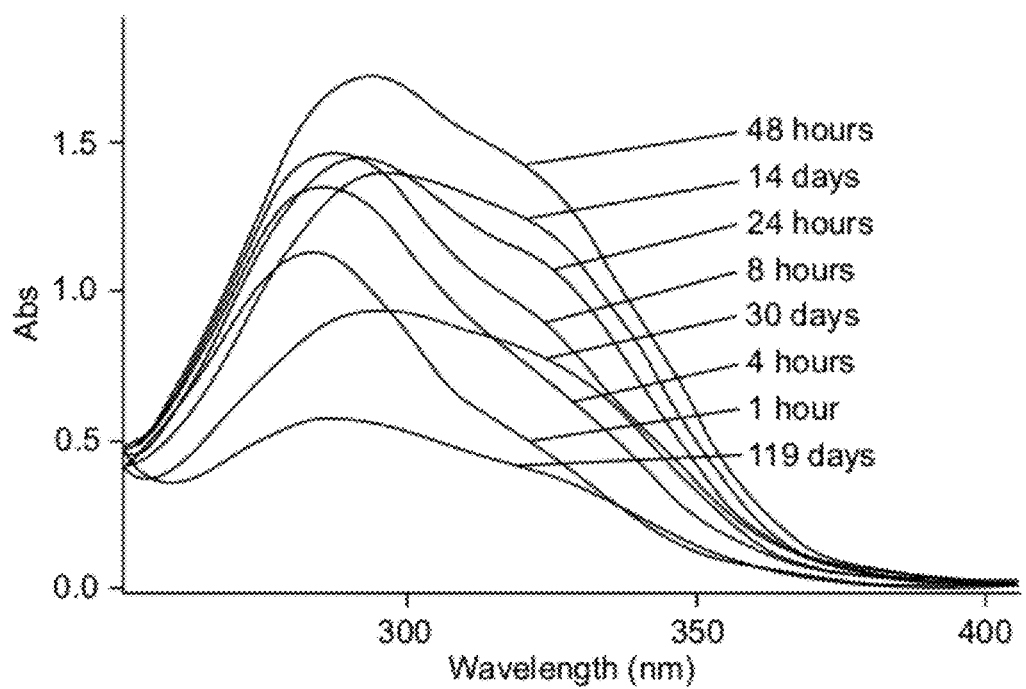
FIG. 2 shows the results of a UV analysis of a water solution of Tetrazene.
Figure 3:
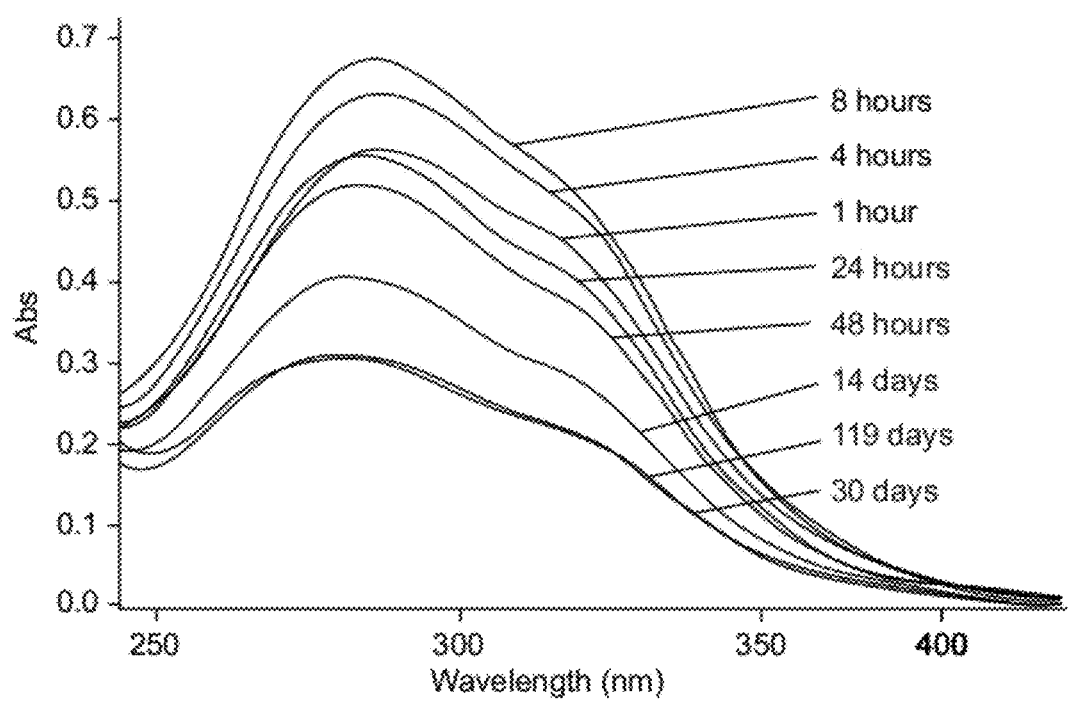
FIG. 3 shows the results of a UV analysis of a water solution of a material prepared according to the present techniques.

As shown in FIG. 2, the Tetrazene sample demonstrates a change in concentration over the first 8 hours and then a bathochromic shift towards 350 nm and increased extinction below 250 nm, which indicates that the material degrades on extended exposure to water. This result would seem to confirm Spears observation of hydrolytic decomposition in Tetrazene. Spears and Elischer, supra. In contrast, as shown in FIG. 3, the UV analysis of MTX-1 would appear to indicate that there is no hydrolytic instability noted for that material, as there seems to be no shift over time. Interestingly, there seems to be a increase in absorbance followed by a decrease, which stabilizes on extended exposure to water. This may be due to some small amount of unstable impurity or a long term equilibration of the pH. At T=119 days, the experiment was discontinued and the suspensions were filtered to give solids corresponding to Tetrazene and MTX-1. Only a small amount of solid remained from the Tetrazene suspension, as most of the material had decomposed to 5-aminotetrazole and an unidentified nitrate-containing material (by FTIR), which subsequently dissolved. In the case of MTX-1, nearly all of the original material was recovered as a solid with <1% decomposing over the 119 day test period. These results indicate that extended storage of MTX-1 under aqueous conditions may be possible.

Figure 4:
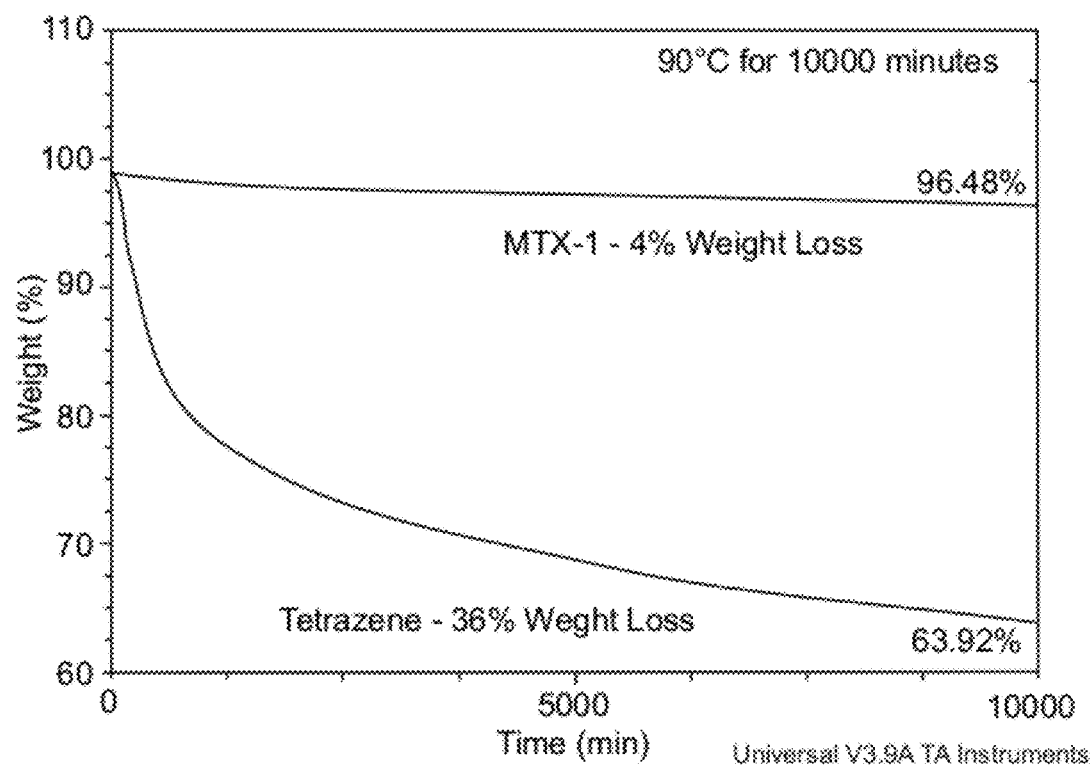
FIG. 4 shows the results of a TGA analysis of Tetrazene and a material prepared according to the present techniques.

The thermal stabilities of Tetrazene and MTX-1 were evaluated by TGA, as shown in FIG. 4. In these experiments, samples of each material were heated to 90° C. and then held at 90° C. for an extended period to evaluate the stability at that temperature. Tetrazene was run for 10000 minutes (167 hrs) and lost 36% by weight over that period, with the majority of the weight loss occurring rapidly in the initial 1000 minutes. An FTIR analysis of the TGA residue indicated a nearly exclusive presence of 5-aminotetrazole, which appears to confirm Bird's fragmentation hypothesis. Bird and Power, supra. MTX-1 was exposed to identical conditions for 18000 minutes (300 hrs) and lost only 4% by weight slowly over that time. These experiments would appear to indicate that MTX-1 has an improved thermal stability over Tetrazene and thus may be appropriate as a Tetrazene replacement if sensitivity requirements are met.

Analysis of sensitivity data for Tetrazene and MTX-1 are shown in Table 1 below. Current analyses include impact, friction, and ESD values for these materials. Evaluation of the data indicates that MTX-1 has impact sensitivity exceeding that of Tetrazene.

TABLE 1

Sensitivity Data for Tetrazene Replacements

| SAMPLE | DSC (20° C./minute) | | IMPACT (J) | FRICTION (grams) | | ESD (mJ) | | TGA % Wt Loss @ 167 hrs |
|---|---|---|---|---|---|---|---|---|
| | Onset | Peak | | No Fire | Low Fire | No Fire | Low Fire | |
| Tetrazene, 1 | 138° C. | 144° C. | 0.021 | 1100 | 1200 | >7.43 | NA | 36.1% |
| MTX-1, 3 | 208° C. | 214° C. | 0.016 | 800 | 900 | 3.30 | 4.18 | 3.5% |

Figure 5:
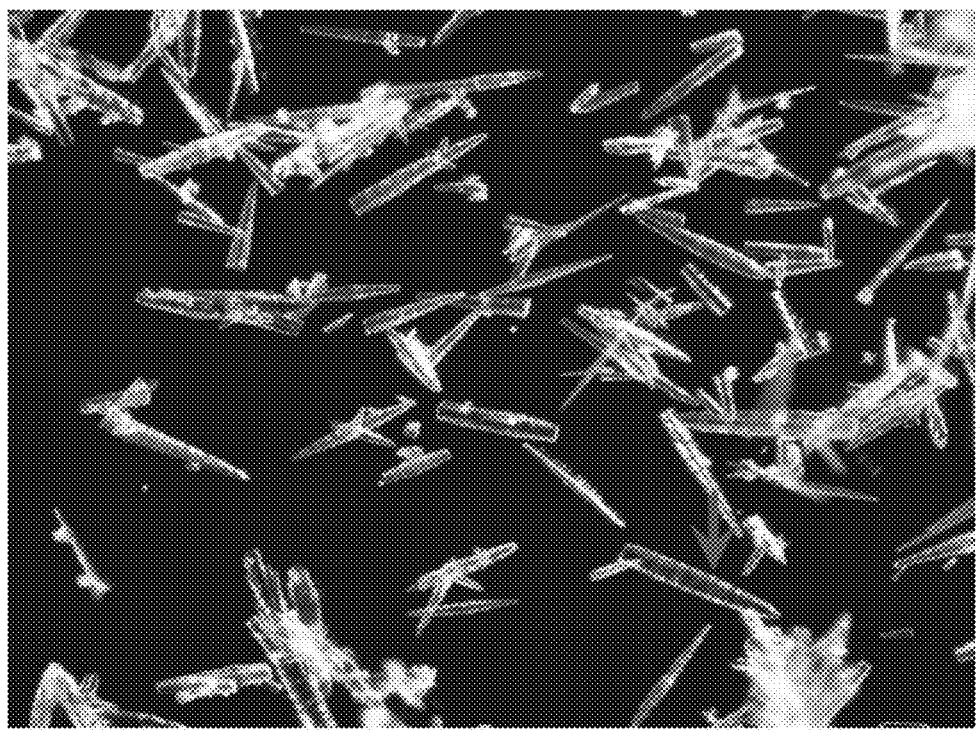
FIG. 5 is an optical photomicrograph taken at 100× magnification of Tetrazene.
Figure 6:
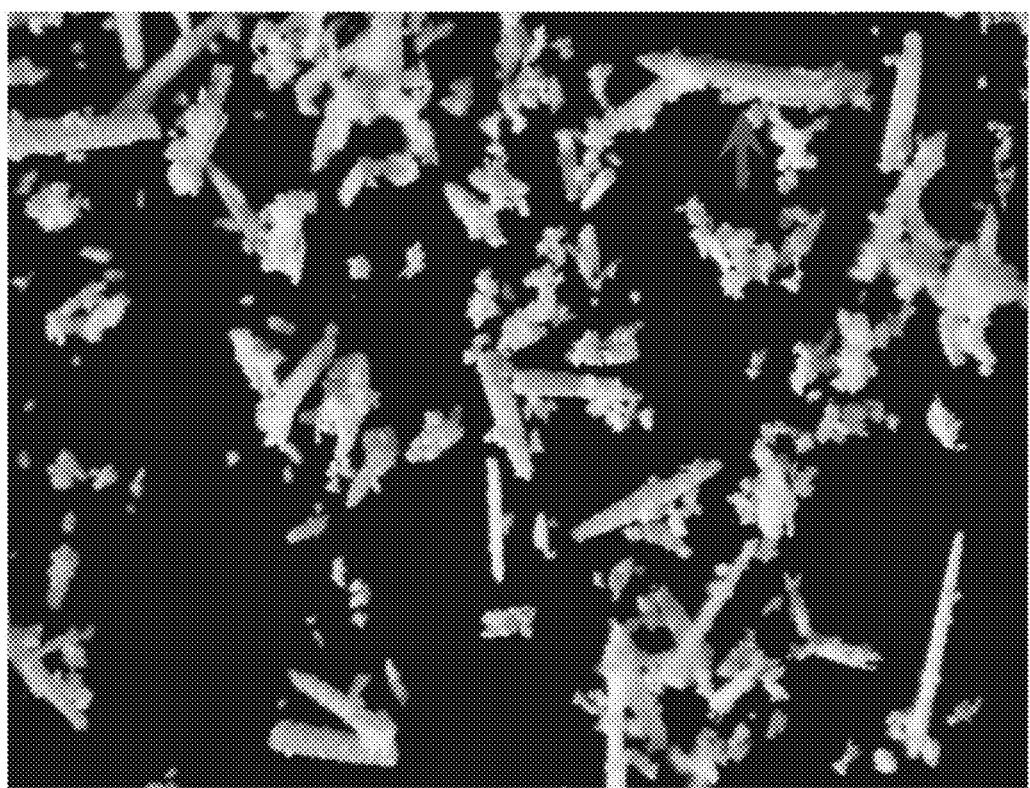
FIG. 6 is an optical photomicrograph taken at 100× magnification of a material prepared according to the present techniques.

Optical photomicrographs of Tetrazene and MTX-1 at 100× magnification are shown in FIGS. 5 and 6, respectively. Comparison of the materials reveals that they have a similar crystal morphology and fracture. As indicated by the arrow shown in each photomicrograph, both materials exhibit long sword-shaped needles that are terminated flat on one end. Crystal fracture occurs parallel to the flat end in both materials.

Figure 7:
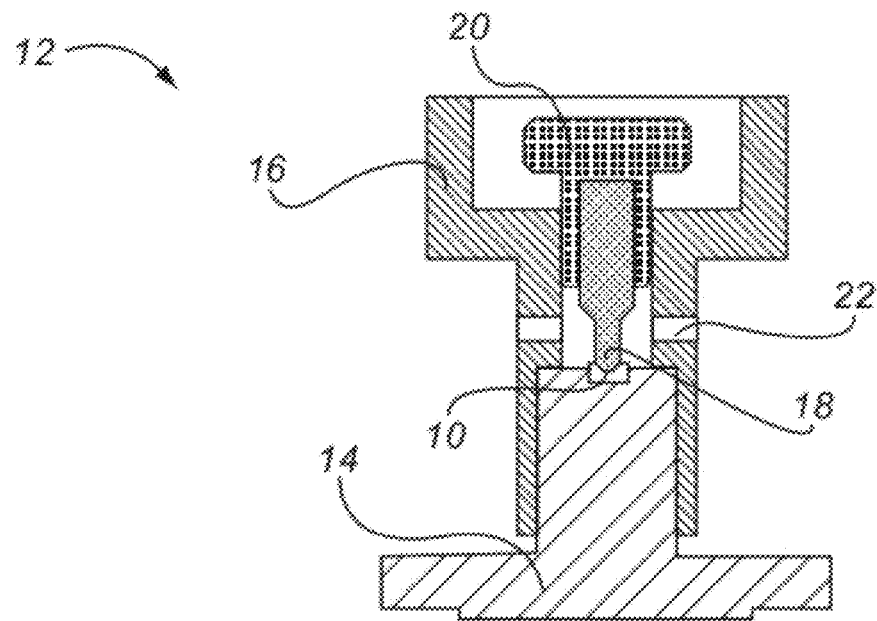
FIG. 7 is a cross-sectional front view of a primer test unit according to one embodiment of the present invention.
Figure 8:
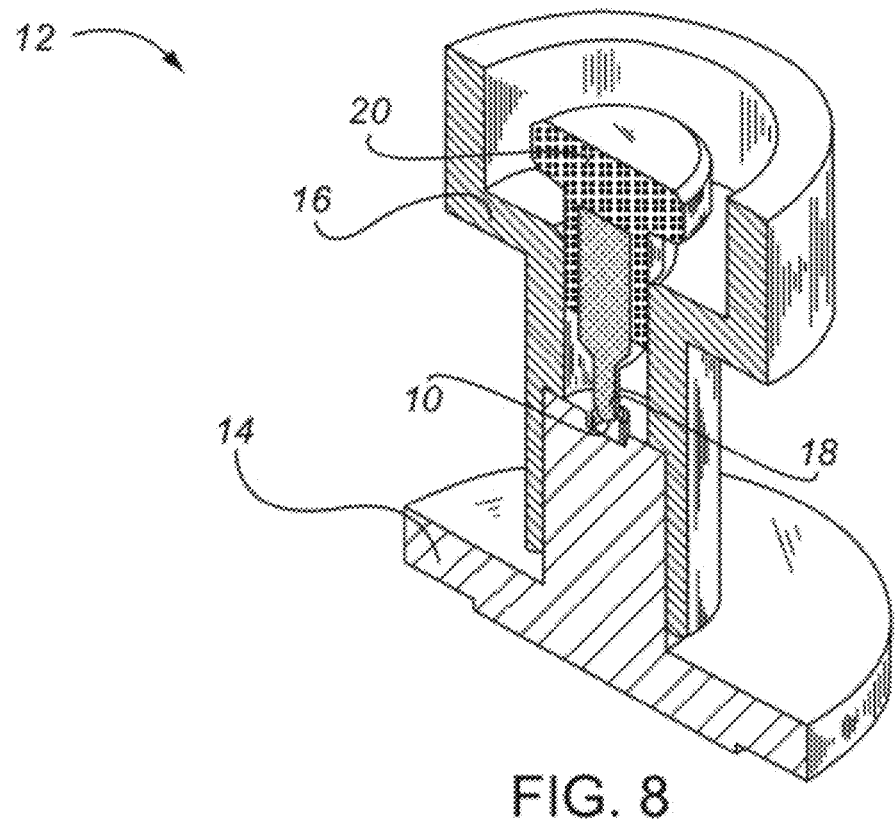
FIG. 8 is a cross-sectional perspective view of the primer test unit of FIG. 7.

Primer Testing:

The ability of these materials to sensitize a primer was evaluated by mixing Tetrazene and MTX-1 with sieved BLS (basic lead styphnate) in a 5:95 ratio and pressing at 10 kpsi into a standard PVU-12 brass primer cup 10. As illustrated in FIGS. 7 and 8, the primer cup 10 was placed into a test unit 12. The test unit 12 comprises a base 14 and a cap 16. A firing pin 18 is positioned above the primer cup 10 within the test unit 12. In this embodiment, the firing pin 18 has a 0.048" diameter with a suitable tip radius. A positioning device 20 is fitted around an opposing end of the firing pin 18 to hold the firing pin 18 in place within the cap 16. In some embodiments, a vent hole 22 is positioned within the cap 16 to form an aperture adjacent the mating surface between the firing pin 18 and the primer cup 10.

When performing testing with this apparatus, powders were prepared utilizing BLS (un-milled,-#100 sieve) as a base material and then adding 5% of the test sensitizer and blending dry on a roller mill for approximately 10 minutes. Both sensitizers, MTX-1 and Tetrazene, were screened through a #40 sieve before adding to the BLS. Handling of these powders was minimized to prevent inhomogeneity based on particle size (settling). Thirty (30) primer cups were loaded with 21±2 mg of BLS alone, BLS/5% Tetrazene and BLS/5% MTX-1 and the powders were pressed into the primer cups with 160 lbs and a 10 second dwell time. The primers (90 total) were stored in a dessicator until tested.

A full 20 unit Neyer analysis was performed on each set of primers utilizing a standard electromagnetic ball-drop primer tester fitted with the above fixture and utilizing a 3.35 oz. stainless steel ball. The firing pin was cleaned after every shot and examined for signs of deterioration, and the pin was replaced with a new pin after every 10 shots. The results for BLS and BLS sensitized with 5% Tetrazene and 5% MTX-1 are shown below in Table 2.

TABLE 2

| Sample | Mu ± σ | 0.001 Level | 0.999 Level |
|---|---|---|---|
| 100% BLS | 12.5" ± 0"* | 12.5* | 12.5* |
| 95% BLS/5% Tetrazene | 4.92" ± 1.41" | 0.56 | 9.28 |

TABLE 2-continued

| Sample | Mu ± σ | 0.001 Level | 0.999 Level |
|---|---|---|---|
| 95% BLS/5% MTX-1 | 5.91" ± 0.42" | 4.60 | 7.21 |

*there was no crossover observed during the BLS analysis

The data indicate that both Tetrazene and MTX-1 act as a sensitizer on BLS pressed into a primer cup with Tetrazene being slightly more efficient. The Tetrazene standard deviation is quite high, however, due to one outlying data point which skewed the Neyer analysis. It is possible that the two materials are nearly equivalent in terms of sensitization and, even if not, MTX-1 is certainly a sensitizer of higher stability.

Tetrazene has been shown to be both thermally and hydrolytically unstable. A potential replacement for this material, MTX-1, exhibits enhanced stability and nearly equivalent sensitization of test primers.

The method of preparation includes introducing Tetrazene into an acid in an amount that is suitable to allow the Tetrazene to become suspended. In some embodiments, the acid is nitric acid. In other embodiments, the acid includes but is not limited to sulfuric acid, perchloric acid, or hydrochloric acid.

A nitrite salt is then added to the suspension, where the reaction temperature is controlled by the addition rate of the nitrite salt. In these embodiments, the nitrite salt is sodium nitrite, where the sodium nitrite may be added as an aqueous solution. In other embodiments, the nitrite salt includes but is not limited to lithium nitrite, potassium nitrite, where the lithium nitrite or potassium nitrite may be added as an aqueous solution.

In some embodiments, the suspension is then stirred at ambient temperature for at least 4 hours. Typically, the suspension is stirred at ambient temperature until the suspension acquires a white appearance.

The suspension may then be filtered to collect the suspension. The suspension is washed with water and dried.

EXAMPLES

The following example demonstrates the preparation and characterization of a material as taught herein.

Figure 9:
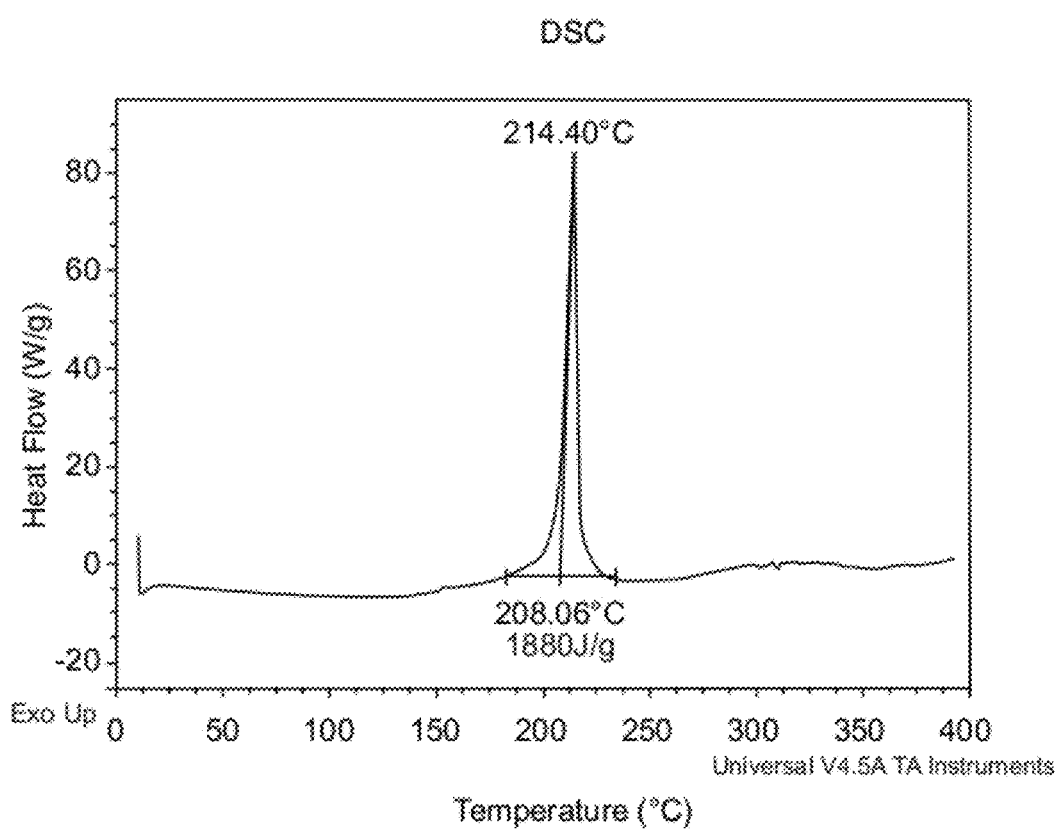
FIG. 9 shows the results of a differential scanning calorimetry analysis of a material prepared according to the present techniques.
Figure 10:
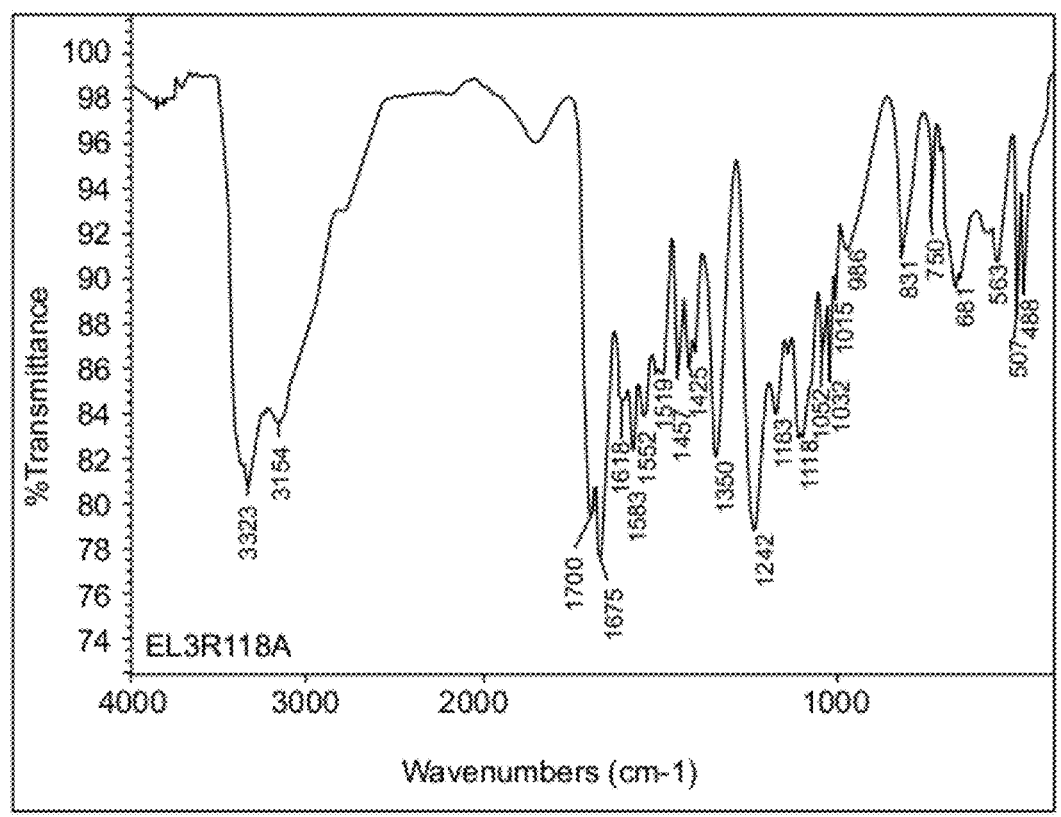
FIG. 10 shows the results of a Fourier transform infrared spectroscopic analysis of a material prepared according to the present techniques.

In this example, Tetrazene (4.53 gms, 24.09 mmol) was suspended in 150 mL of 1N $HNO_3$ in a 250 mL beaker and magnetically stirred at 400 RPM. The beaker was placed in a room temperature water bath that would act as a heat sink. A solution of NaNO$_2$ (2.50 gms, 1.50 eq.) dissolved in 30 mL of water was added over approximately 10 minutes at a constant rate to keep the reaction temperature from increasing. Some effervescence was noted during the addition. The mixture was stirred at ambient temperature for 4.5 hours during which the initial wheat colored suspension turned white. The white suspension was filtered over Whatman #1 filter paper, washed with water (3 times) and dried in a convection oven at 65° C. for 2 hours. Yield: 3.13 gms (66%). The collected material was then analyzed by differential scanning calorimetry ("DSC"), the results of which are shown in FIG. 9. The collected material was also analyzed by Fourier transform infrared ("FTIR") spectroscopic analysis, the results of which are shown in FIG. 10.

The foregoing is provided for purposes of illustrating, explaining, and describing embodiments of the present invention. Further modifications and adaptations to these embodiments will be apparent to those skilled in the art and may be made without departing from the scope or spirit of the invention.

That which is claimed is:

1. A composition comprising MTX-1.

2. The composition of claim 1, wherein the composition is used as a replacement for tetrazene.

3. A compound comprising MTX-1.

4. The compound of claim 3, wherein the compound is used as a replacement for tetrazene.

5. A compound having a formula:

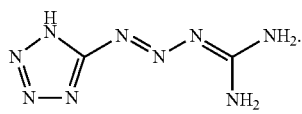 [SMILES: NC(N)=N/N=N/c1nnn[nH]1]

6. The compound of claim 5, wherein the compound is used as a replacement for tetrazene.

7. A product formed by
   (a) combining tetrazene and an acid to form a suspension; and
   (b) adding a nitrite salt to the suspension;

which exhibits substantially the same differential scanning calorimetry curve as depicted in FIG. 9.

8. A product formed by
   (a) combining tetrazene and an acid to form a suspension; and
   (b) adding a nitrite salt to the suspension;

which exhibits substantially the same Fourier transform infrared spectroscopy spectra as depicted in FIG. 10.

9. A reaction product of:
   (a) tetrazene;
   (b) an acid; and
   (c) a nitrite salt;

wherein the reaction product exhibits substantially the same Fourier transform infrared spectroscopy spectra as depicted in FIG. 10.

10. The reaction product of claim 9, wherein the acid is nitric acid, sulfuric acid, perchloric acid, or hydrochloric acid.

11. The reaction product of claim 9, wherein the nitrite salt is sodium nitrite, lithium nitrite, potassium nitrite, an aqueous solution of sodium nitrite, an aqueous solution of lithium nitrite, or an aqueous solution of potassium nitrite.

* * * * *